United States Patent [19]

König

[11] Patent Number: 4,506,668

[45] Date of Patent: Mar. 26, 1985

[54] INSULATED SLEEVE HIGH FREQUENCY RESECTOSCOPE

[75] Inventor: Helmut König, Diemelstadt, Fed. Rep. of Germany

[73] Assignee: Olympus Winter & Ibe GmbH, Hamburg, Fed. Rep. of Germany

[21] Appl. No.: 505,999

[22] Filed: Jun. 20, 1983

[30] Foreign Application Priority Data

Jun. 23, 1982 [DE] Fed. Rep. of Germany ....... 3223361

[51] Int. Cl.$^3$ ............................................. A61B 17/32
[52] U.S. Cl. ............................................... 128/303.15
[58] Field of Search ........... 128/303.1, 303.14, 303.15, 128/303.17

[56] References Cited

U.S. PATENT DOCUMENTS

| | | | |
|---|---|---|---|
| 3,768,482 | 10/1973 | Shaw | 128/303.14 X |
| 4,030,502 | 6/1977 | Iglesias | 128/303.15 |
| 4,060,086 | 11/1977 | Storz | 128/303.15 |

Primary Examiner—Edward M. Coven
Attorney, Agent, or Firm—Walter C. Farley

[57] ABSTRACT

The insulating end piece of a high frequency cutting loop resectoscope is formed using ceramic fibers in an epoxy resin matrix for improved strength, heat dissipation and abrasion resistance. An end portion has fibers fused together or a separate annular ceramic body welded to the fibers.

14 Claims, 2 Drawing Figures

4,506,668

INSULATED SLEEVE HIGH FREQUENCY RESECTOSCOPE

This invention relates to a high frequency loop resectoscope having a shaft or sleeve with an insulated end.

BACKGROUND OF THE INVENTION

In the movement region of a loop resectoscope adjacent the high frequency cutting loop, it is known to provide the end of the resectoscope sleeve with a sleeve portion formed from an electrical insulating material to avoid the possibility of electrical short circuits caused by contact between the sleeve and the loop, which is energized with a high frequency voltage, and which can come in contact with the sleeve. Such insulating pieces are customarily produced from a glass fiber-reinforced plastic which has rigidity of form and which is break-resistant to a reasonable degree.

The poor temperature resistance of this insulating material is, however, a disadvantage. Considerable thermal damage to the plastic can result, especially at the region of the distal edge of 2the insulating piece with which the still-energized loop very frequently comes into contact at very high temperatures, necessitating frequent replacement of the insulating portion or the entire shaft.

One structure of the general type with which the invention is concerned is shown in German OS No. 25 02 863 and U.S. Pat. No. 4,060,086 in which an effort has been made to avoid the kind of damage discussed above by providing a ceramic insert sleeve encased in an outer plastic sleeve of the insulating portion. The highly heat-resistant ceramic material is intended to be sufficiently temperature resistant and, by thermal insulation, is intended to protect the surrounding plastic against overheating and, in turn, the plastic is intended to ensure break resistance.

This structure has the disadvantage, however, of being extraordinarily expensive. In addition, it should be noted that the thermal insulating characteristics of ceramic are not sufficient under all circumstances to prevent the plastic material surrounding it from temperature damage. Thus, detachment of the ceramic insert and resulting destruction of the insulating piece can occur. In addition, the protection of the solid-body ceramic sleeve against splintering is not sufficient. In the event of inexpert handling of the device, and especially in the event of compression of the insulating piece, the ceramic insert can be shattered.

BRIEF SUMMARY OF THE INVENTION

Accordingly, an object of the present invention is to provide a resectoscope of the type having a sleeve with an insulating end portion wherein the insulating portion is provided with a section which is largely insensitive to contact by the hot high frequency loop, has high break resistance and which can be produced at reasonable production cost.

Briefly described, the invention comprises a high frequency cutting loop resectoscope of the type having a sleeve and a loop which is movable relative to a portion of the sleeve for engaging and excising tissue therebetween, the distal end portion of the sleeve being formed from an electrical insulating material, wherein the improvement comprises forming at least a portion of said distal end of said sleeve in the area most closely approached by said loop from a polymeric body including fibers of a highly heat resistant and abrasion resistant ceramic material of high thermal conductivity.

In order that the manner in which the foregoing and other objects are attained in accordance with the invention can be understood in detail, particularly advantageous embodiments thereof will be described with reference to the accompanying drawings, which form a part of this specification, and wherein:

FIG. 1 is a partial side elevation, somewhat enlarged, and in partial section, of one embodiment of a resectoscope in accordance with the present invention; and FIG. 2 is a partial side elevation, in partial section, of a second embodiment of a resectoscope in accordance with the present invention.

DETAILED DESCRIPTION OF PREFERRED EMBODIMENTS

Figure 1:
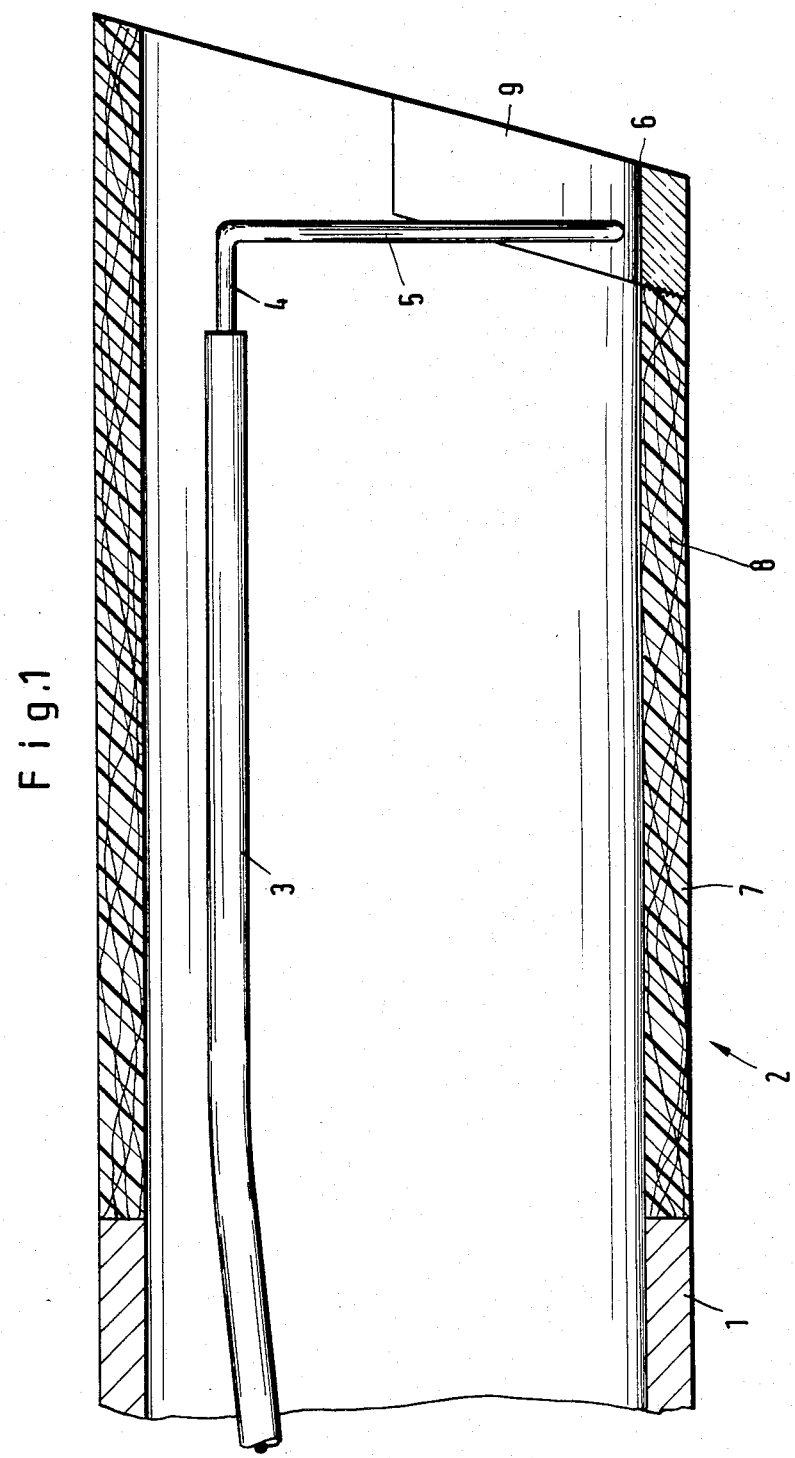

As shown in FIG. 1, the working end of a resectoscope incorporating the present invention includes a metallic tubular shaft 1 which is fixedly attached to an electrical insulating body indicated generally at 2, the distal end of which is inclined with respect to the axis of the tube and has a continuous portion which is somewhat in the shape of a beak. Within tube 1 is shown the distal end of a cutting loop including electrically insulated loop carriers 3 through which extends feed conductors 4 for the loop 5. The loop portion of the apparatus is quite conventional in the sense that the loop is a generally U-shaped or semicircular loop of wire, the two upper ends of which are connected to generally parallel feed conductors 4 which pass through insulated loop carrier portions. The semicircular portion of the loop conforms generally to the inside diameter of the tubular shaft 1, 2, the loop being extendable somewhat beyond the distal end of the shaft and retractable so that when it comes back into the insulating piece 2 it fits closely against the inside wall. The loop 5 is thus advanceable somewhat beyond the proximal terminal position shown in the figure and can extend far beyond the insulating piece 2.

Sliding contact between the loop and the inside wall of the insulating piece is required, for one reason, in order to keep the central interior space of the shaft pipe free to the maximum extent possible for a lens usually inserted therein so that the surgical procedure being performed can be observed. Essentially, however, in this kind of loop and shaft arrangement, there develops a scissor-like cutting effect at the distal forward edge 6 of the insulating member upon retraction of the loop into the insulating piece which is made use of for the precise severing of pieces of tissue.

High frequency cutting loops, such as the loop 5 shown, are supplied with high frequency electrical energy through feed conductors 4. The grounding of the patient represents the other terminal of the circuit. Thus, high frequency current flow occurs from loop 5, the flow of current at a distance from the loop being at a harmlessly low level but, in the immediate vicinity of the loop the current density is highly concentrated and there creates a considerable rise in temperature. A region of very high temperature develops around the surface of the loop accompanied by a light arc. In this way, the loop acts to cut tissue.

When cutting tissue with a loop bent in the form of a semi-circle from the tissue, for example, of the prostate, one strip after another is removed somewhat like a series of chips wherein the loop is first moved somewhat beyond the end of a tube, then energized and pulled back, cutting through the tissue. The loop then comes into contact with the forward edge 6 of the insulating piece, fitting closely at that point to accomplish the cutting effect described. Then, the high frequency current is turned off.

The forward edge 6 is thus subject almost continuously, or at least for long times, to very high temperatures in an area of the shape of a semi-arc against which the cutting loop 5 fits closely. Because of this, the forward edge 6 is under considerable strain. Whenever the cutting loop 5 is pulled back into the insulating piece in the rearward terminal position shown in the figure, it is deenergized, when properly used by an accomplished manipulator, so that in this location the temperature load is relieved. Furthermore, in this area, even when the loop is energized, the temperatures are lower since, because of the electrical insulating effect from the body by the insulating piece 2, a circuit no longer exists and the high frequency current, if any, is substantially lower.

In accordance with the invention, the detrimental effect of the high temperature on the insulating piece which exists particularly in the semicircularly shaped portion 6 of the distal edge, is counteracted by forming the insulating piece 2 from a polymeric plastic matrix 7 with embedded fibers 8 of a high heat-resistant ceramic material having high thermal conductivity characteristics. The fibers are embedded in the plastic material in a known manner, as is known from glass fibers, and they can be provided in the form of mats of fabric or wound threads or, alternatively, the fibers can be substantially unstructured as in the form of fleece or admixed fibers. This results in considerably increased structural strength of the polymeric material as a result of which the entire plastic body becomes extraordinarily break resistant and holds its shape very well.

Whenever the hot cutting loop 5 comes into contact with the insulating piece 2, the plastic is most likely to be damaged in the uppermost surface area extending up to the next ceramic fiber. The heat which would otherwise cause damage upon contact of the high temperature cutting loop is conducted away extremely effectively by the ceramic fibers so that even at a very short distance from the cutting loop a lower temperature, which is sufficiently low to be harmless to the plastic matrix, exists in the insulating piece 2.

In the embodiment shown by way of example, the lower part of the distal edge 6 of the insulating piece 2, acted upon by the cutting loop, is made from a different material in the region of the half-ring 9 than the remainder of the insulating piece. This half-ring 9 which can, alternatively, be formed as a total ring extending around the entire edge of piece 2, can be formed in essentially two ways. In one embodiment it can be prefabricated as a fully ceramic body and can be bonded or melted onto the fibers 8 of the insulating piece. In this arrangement the result is particularly effective thermal protection in the forward edge area of the insulating piece with a very firm mechanical connection with the insulating piece and a high degree of protection against mechanical damage.

In a particularly suitable manner, the half-ring 9 can be produced by melting or sintering together of the distal ends of the fibers 8. The melted-together or sintered piece 9 may be more or less rich in hollow spaces. Preferably, a narrow, melted-together edge area is developed free of hollow spaces resulting in an area which is thin and thus of low break sensitivity, has great abrasion strength, and can be put under a high thermal load. This molten-together area continuously passes over or merges into the individual fibers within portion 8 and, as a result, is attached to the remainder of insulating piece 2 with great strength.

In this sense, the region illustrated as a separate piece can, alternatively, be formed from the same material as the rest of the insulating piece, the illustrated separation thus indicating simply a region which has been differently treated.

Figure 2:
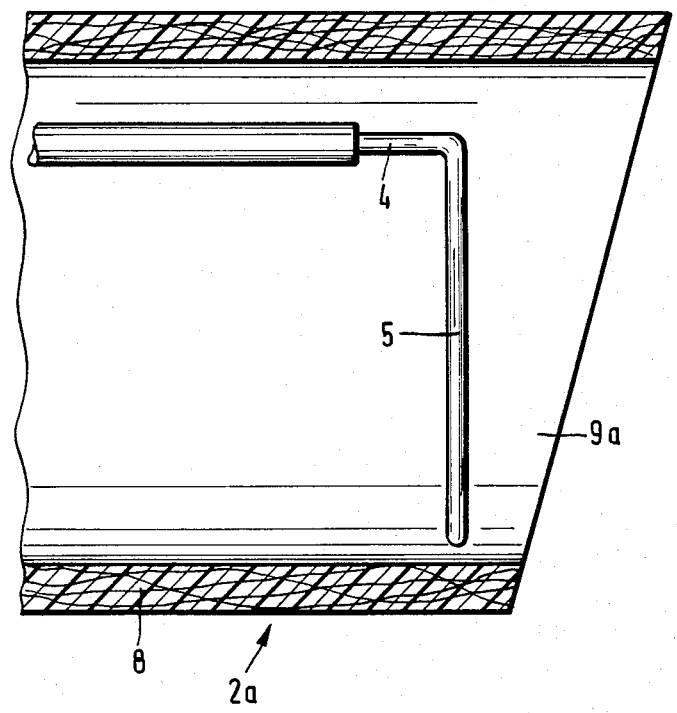

FIG. 2 shows an alternative embodiment in which the end portion 9a of insulating piece 2a is no different from the remainder of the insulating piece, i.e., the entire piece is formed from a cured polymeric material with embedded ceramic fibers having high heat resistance and abrasion resistance and having high thermal conductivity.

A large number of materials can be employed as the ceramic material including, for example, fibers of silicon carbide, boron carbide and aluminum oxide ($Al_2O_3$). These materials are extraordinarily hard and, thus, abrasion resistant and they also have high heat conductivity with good fiber flexibility. In experiments, highly purified aluminum oxide has been found to be particularly suitable. Such materials have a heat conductivity coefficient which lies in the order of magnitude of the conductivity of metals and corresponds to approximately the heat conductivity of cast iron. For the plastic matrix, epoxy resins have been found to be suitable and can be thermally loaded up to about 200° C.

The arrangement of the ceramic fibers or threads 8, which are illustrated in the figures in plastic matrix 7, would seem to suggest that only a few threads exist, but this is only for simplicity in the drawing. Preferably, higher density packing is used with a considerably greater number of threads than indicated.

The ceramic threads, webs produced from them or unwoven fibers can be processed largely without difficulty and in a fashion similar to corresponding glass materials formed in a plastic matrix into any kind of shaped bodies, the techniques being such that the production costs remain relatively low. According to the invention, a highly heat-resistant ceramic of high thermal conductivity is to be used. As a result of that, good heat conductivity in the insulating piece results with the heat being immediately conducted away from the surface area in contact with the hot, high-frequency cutting loop. Temperature damage is thereby avoided or is minimized and limited to the immediate surface area. In this case, use is made of the fact that the heat conductivity of certain suitable ceramics is higher by at least an order of magnitude than that of glass and lies approximately in the order of magnitude of metals. As compared with the known developments of insulating pieces with glass fiber-reinforced plastic, the wear resulting from the use of the high frequency loop is less by orders of magnitude. As compared with known constructions with inserted protective ceramic pipe, the advantages of more favorable production costs as well as greater break resistance and better temperature stability result from the more homogenous connection of the materials.

As will be recognized from the foregoing description, the distal marginal area of the insulating piece 2, 2a is exposed to special abrasion and thermal strains as a result of the cutting loop being conducted past at high temperature in this area during each cutting step. In the development of this marginal area of melt-connected fibers which can be fused or sintered together, there results considerable increase in the strength and a decrease in the quantity of plastic material. Because this melted-together marginal area is homogenously connected with the fibers extending from the remainder of the insulating piece and is formed rather narrowly, high mechanical strength results.

While certain advantageous embodiments have been chosen to illustrate the invention, it will be understood by those skilled in the art that various changes and modifications can be made therein without departing from the scope of the invention as defined in the appended claims.

What is claimed is:

1. A high frequency cutting loop resectoscope of the type having a sleeve and a loop which is movable relative to a portion of the sleeve for engaging and excising tissue therebetween, the distal end portion of the sleeve being formed from an electrical insulating material, wherein the improvement comprises
    forming at least a portion of said distal end of said sleeve in the area most closely approached by said loop from a polymeric body including means comprising fibers of a highly heat resistant and abrasion resistant ceramic material of high thermal conductivity for conveying heat away from the end of said sleeve and to the surrounding material to dissipate the damaging effect of the heat at said end.

2. A device according to claim 1 wherein said portion of said distal end includes a fabric of fibers of ceramic material in a cured resin matrix.

3. A device according to claim 2 wherein said fibers are welded to the adjacent marginal arc of said sleeve.

4. A device according to claim 1 wherein said ceramic fibers consist essentially of a material selected from the group including silicon carbide, boron carbide and aluminum oxide.

5. A device according to claim 1 wherein said portion of said distal end includes a mass of randomly oriented ceramic fibers embedded in a cured resin matrix.

6. A device according to claim 5 wherein said ceramic fibers consist essentially of a material selected from the group including silicon carbide, boron carbide and aluminum oxide.

7. A device according to claim 5 wherein said fibers are welded to the adjacent marginal arc of said sleeve.

8. A device according to claim 1 wherein said sleeve comprises ceramic fibers in a resin matrix and wherein said portion of said distal end includes an annularly shaped ceramic body welded to said ceramic fibers in the marginal area adjacent said body.

9. A device according to claim 8 wherein said ceramic fibers consist essentially of a material selected from the group including silicon carbide, boron carbide and aluminum oxide.

10. An improved high frequency cutting loop resectoscope of the type having a sleeve and a loop which is movable relative to a portion of the sleeve for engaging and excising tissue therebetween, the distal end portion of the sleeve being formed from an electrical insulating material, wherein the distal end portion of said sleeve comprises a polymeric body containing means comprising fibers of a highly heat resistant and abrasion resistant ceramic material of high thermal conductivity for carrying away and dissipating heat produced at said portion of said sleeve as said loop is moved adjacent thereto.

11. A device according to claim 10 wherein said distal end portion includes a fabric of fibers of ceramic material in a cured resin matrix.

12. A device according to claim 10 wherein said ceramic fibers consist essentially of a material selected from the group including silicon carbide, boron carbide and aluminum oxide.

13. A device according to claim 10 wherein said distal end portion includes a mass of randomly oriented ceramic fibers embedded in a cured resin matrix.

14. A device according to claim 13 wherein said ceramic fibers consist essentially of a material selected from the group including silicon carbide, boron carbide and aluminum oxide.

* * * * *